United States Patent
Ghosh et al.

(10) Patent No.: US 6,187,303 B1
(45) Date of Patent: Feb. 13, 2001

(54) HAIR CONDITIONING COMPOSITION

(75) Inventors: Dipak K. Ghosh, Woodridge; Rose A. Casanova-Gugliotta, Chicago; Natalya Gurman, Buffalo Grove, all of IL (US)

(73) Assignee: Alberto-Culver Company, Melrose Park, IL (US)

(*) Notice: Under 35 U.S.C. 154(b), the term of this patent shall be extended for 0 days.

(21) Appl. No.: 09/309,905

(22) Filed: May 11, 1999

(51) Int. Cl.$^7$ .................................................. A61K 7/06
(52) U.S. Cl. .................................. 424/70.1; 514/880
(58) Field of Search ................... 424/70.1–70.6; 514/880–881

(56) References Cited

U.S. PATENT DOCUMENTS

| | | | |
|---|---|---|---|
| 4,102,795 | 7/1978 | Minegishi et al. | 252/8.9 |
| 4,183,917 | 1/1980 | Iwao et al. | 424/70 |
| 4,552,754 | 11/1985 | Muramatsu et al. | 424/70 |
| 4,690,817 | 9/1987 | Davis et al. | 424/70 |
| 4,765,975 * | 8/1988 | Iovanni et al. | 424/70 |
| 4,784,844 | 11/1988 | Thimineur et al. | 424/65 |
| 4,837,005 | 6/1989 | Brode, II et al. | 424/47 |
| 5,051,250 | 9/1991 | Patel et al. | 424/70 |
| 5,068,324 | 11/1991 | O'Lenick, Jr. | 540/471 |
| 5,100,655 | 3/1992 | Takano et al. | 424/63 |
| 5,213,716 | 5/1993 | Patel et al. | 252/547 |
| 5,225,112 | 7/1993 | Miyazawa et al. | 252/545 |
| 5,346,642 | 9/1994 | Patel et al. | 252/174.21 |
| 5,599,483 | 2/1997 | Mizushima et al. | 510/119 |
| 5,696,069 | 12/1997 | Ito et al. | 510/123 |
| 5,696,070 | 12/1997 | Tachizawa et al. | 510/123 |
| 5,866,040 | 2/1999 | Nakama et al. | 252/312 |

FOREIGN PATENT DOCUMENTS

| | | |
|---|---|---|
| 5-178731 | 7/1993 | (JP) . |
| 8-193020 | 7/1996 | (JP) . |
| 9-100216 | 4/1997 | (JP) . |

OTHER PUBLICATIONS

Abstract—Ventura et al., "Identification of Surfactants in Water by FAB Mass Spectrometry", Water Res (1989), 23(9), 1991–1203.

* cited by examiner

Primary Examiner—Shelley A. Dodson
Assistant Examiner—Konata M. George
(74) Attorney, Agent, or Firm—Leydig, Voit & Mayer, Ltd.

(57) ABSTRACT

An aqueous hair conditioning composition is disclosed. The composition includes stearalkonium chloride and a stabilizing component comprising a polyoxyethylene glycol ether of stearyl alcohol, such as, for example, polyoxyethylene (21) stearyl ether. The polyoxyethylene stearyl ether is provided in an amount sufficient to inhibit precipitation of stearalkonium chloride in the composition. Also disclosed are a method of conditioning hair and a method of inhibiting precipitation of a stearalkonium chloride in an aqueous cosmetic hair conditioning composition.

37 Claims, No Drawings

HAIR CONDITIONING COMPOSITION

TECHNICAL FIELD OF THE INVENTION

The present invention relates generally to cosmetic hair conditioning compositions. In particular, the present invention relates to an aqueous hair conditioning composition with improved stability.

BACKGROUND OF THE INVENTION

It is well known that hair conditioning compositions are desired by consumers because of their ability to minimize fly away, static charge, and tangling of the hair, and also because they soften hair and facilitate combing. Typically, hair conditioning formulations contain, as an active ingredient, a quaternary ammonium compound in which the molecular structure includes a nitrogen joined to four organic groups (i.e., the cation) and a negatively charged acid radical (i.e., the anion). For example, a particularly desirable active agent in hair conditioning compositions is stearalkonium chloride ($C_{27}H_{50}NCl$), of the following formula:

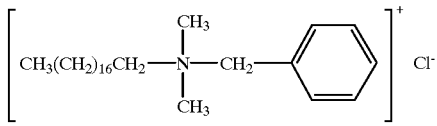

Despite the conditioning attributes provided by stearalkonium chloride, it has proven to be very difficult in practice to implement stearalkonium chloride in hair conditioning compositions because of the drawbacks associated therewith. For example, stearalkonium chloride is susceptible to precipitation in conventional hair conditioning formulations, thereby causing an undesirable "pearlized effect." In this respect, while conventional stearalkonium chloride-containing hair conditioning compositions may have a creamy appearance initially and be aesthetically pleasing to consumers, over a period of weeks (depending upon storage and temperature conditions) stearalkonium chloride crystallizes out and the appearance of the composition deteriorates and becomes more pearly. The pearly appearance is itself undesirable to consumers. The inconsistency in appearance (even from one bottle to the next) exhibited by these conventional stearalkonium chloride-containing hair conditioning compositions is especially undesirable and troubling to consumers.

The pearlizing effect also adversely affects the selected color of tinted hair conditioners. For example, if the hair conditioning composition is initially colored (e.g., red or pink), over time the composition will appear to have faded since the white background is modified by virtue of the pearlizing effect. This perception of color fading also negatively impacts the consumer. Heretofore, it has proven to be very difficult to provide a stearalkonium chloride-containing hair conditioning composition in which the stearalkonium chloride does not precipitate such that the composition maintains a relatively consistent appearance and/or color over time.

Accordingly, it will be appreciated that there exists a need in the art for a stearalkonium chloride-containing hair conditioning composition that does not suffer from the undesirable pearlizing effect and whose appearance and color remain stable over time. It is an object of the present invention to provide such a hair conditioning composition that achieves these needs. These and other objects and advantages of the present invention, as well as additional inventive features, will be apparent from the description of the invention provided herein.

BRIEF SUMMARY OF THE INVENTION

The present invention provides a hair conditioning composition which is stable both to a pearlizing effect and in appearance. The composition of the present invention comprises water, stearalkonium chloride, and a stabilizing component to inhibit pearlizing. The stabilizing component comprises a polyoxyethylene stearyl ether having a sufficient number of oxyethylene units to be capable of inhibiting the precipitation of stearalkonium chloride in the composition when the polyoxyethylene stearyl ether is present in the composition in an amount sufficient to inhibit the precipitation (e.g., crystallization) of the stearalkonium chloride.

Other aspects of the present invention include a method of conditioning hair and a method of inhibiting the precipitation of a stearalkonium chloride in an aqueous cosmetic hair conditioning composition, respectively. The method of conditioning hair comprises contacting the hair with an aqueous composition that includes a stearalkonium chloride and a stabilizing component comprising a polyoxyethylene stearyl ether as described above. The method of inhibiting the precipitation of a stearalkonium chloride in an aqueous cosmetic hair conditioning composition includes adding to the composition a polyoxyethylene stearyl ether having a sufficiently high molecular weight such that it is capable of inhibiting the precipitation of stearalkonium choloride when it is added in an amount sufficient to inhibit the precipitation of the stearalkonium chloride.

Advantageously, the present invention permits the inclusion of a stearalkonium chloride in a conditioning composition, thereby enhancing the conditioning properties thereof, without causing the formation of an undesirable precipitate. As such, the present invention also provides a conditioner that is stable, relatively uniform in appearance, and aesthetically pleasing.

DETAILED DESCRIPTION

The present invention is predicated, at least in part, on providing an aqueous hair conditioning composition that includes both stearalkonium chloride and a polyoxyethylene glycol ether of stearyl alcohol. Surprisingly, in accordance with the present invention, by adjusting the number of polyoxyethylene units in the polyoxyethylene stearate ester, it has been found that precipitation of stearalkonium chloride in the inventive composition is inhibited or precluded. By way of example, in one embodiment, the polyoxyethylene stearate ester is polyoxyethylene (21) stearyl ether.

In particular, the inventive hair conditioning composition is aqueous. In this respect, the amount of water (diluent) in the composition can be from about 10% to about 90% by weight of the composition, preferably from about 40% to about 90% by weight of the composition, even more preferably from about 60% to about 90% by weight of the composition, and still more preferably from about 75% to about 80% by weight of the composition.

The active conditioning ingredient in the inventive hair conditioning composition is stearalkonium chloride. Preferably, the amount of stearalkonium chloride present in the composition ranges from about 0.2% to about 5% by weight of the composition, more preferably from about 0.5% to about 2.5% by weight of the composition, and even more preferably from about 0.75% to about 1.5% by weight of the composition. It is to be noted that the ranges set forth herein are calculated with respect to a 100% active concentration of the ingredients. As a result, if, for example, the stearalkonium chloride is provided in a form in which the active form of the stearalkonium chloride is only in a concentration of 25%, then, of course, it is desirable to use 4 times the amounts set forth in these ranges.

The present invention also includes a stabilizing component in the form of a polyoxyethylene stearyl ether. The polyoxyethylene stearyl ether is represented by the following formula:

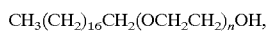

$$CH_3(CH_2)_{16}CH_2(OCH_2CH_2)_nOH,$$

wherein n is greater than 2. Significantly, the polyoxyethylene stearyl ether contains a sufficient number of oxyethylene units (identified as "n" in the formula) to stabilize the composition against precipitation of stearalkonium chloride. Desirably, the number of polyoxyethylene units is greater than 2, preferably at least 5, more preferably at least 10, even more preferably at least 15, and still more preferably 20 or more. In a preferred embodiment, the polyoxyethylene stearyl ether is polyoxyethylene (21) stearyl ether (such that n is 21). Polyoxyethylene (21) stearyl ether is commercially available from ICI Surfactants of Wilmington, Del., under the trade name Brij 721 S.

The polyoxyethylene stearyl ether is provided in the composition in an amount sufficient to inhibit precipitation of stearalkonium chloride in the composition. For example, polyoxyethylene stearyl ether is provided in an amount ranging from about 0.1% to about 10% by weight of the composition, more preferably in an amount ranging from about 0.1% to about 4% by weight of the composition, and even more preferably in an amount ranging from about 0.35% to about 1% by weight of the composition. Desirably, the ratio of stearalkonium chloride to polyoxyethylene stearyl ether is from about 4:1 to about 1:1.

Although not essential, at least one preservative in any effective amount is useful in preferred hair conditioning compositions of the invention. Examples of suitable preservatives include, for example, disodium EDTA, trisodium EDTA, tetrasodium EDTA, DMDM hydantoin, and combinations thereof. As will be appreciated by one of ordinary skill in the art, DMDM hydantoin is understood worldwide pursuant to the nomenclature for cosmetic products set forth in the International Cosmetic Ingredient Directory and Handbook. The chemical name for DMDM hydantoin is 1,3-dimethylol-5,5-dimethyl hydantoin, which is commercially available from Lonza, Inc. of Fairlawn, N.J. under the trade name "Glydant." In one embodiment, the preservative includes disodium EDTA and DMDM hydantoin in combination. Preferably, the preservative is provided in an amount of from about 0.1% to about 0.5% by weight of the composition, preferably from about 0.2% to about 0.3% by weight of the composition.

The inventive hair conditioning composition can also include, optionally, at least one thickener, if desired. The thickener, if used, enhances the viscosity of the hair conditioning composition and facilitates combing, especially with wet hair. The thickener can be, for example, in the form of any of a number of suitable alcohols, as will be appreciated readily by one of ordinary skill in the art. Especially suitable thickeners include, but are not limited to, stearyl alcohol, cetyl alcohol, and combinations thereof. The thickener is desirably present in the composition in an amount ranging from about 0.5% to about 11% by weight, more preferably from about 1% to about 5% by weight, and even more preferably from about 1.2% to about 3.0% by weight of the composition. In preferred embodiments, the thickener includes both stearyl alcohol and cetyl alcohol. In these embodiments, the amount of stearyl alcohol is preferably from about 0.5% to about 5% by weight, more preferably, from about 1% to about 2.5% by weight, and even more preferably from about 1.2% to about 1.5% by weight of the composition; while the amount of cetyl alcohol is preferably from about 0.5% to about 10% by weight, more preferably from about 1% to about 5% by weight, and even more preferably, from about 2% to about 3% by weight of the composition.

Other optional ingredients that may be useful in the hair conditioning compositions of the present invention include opacifiers, hair strengtheners, fragrances, and/or dyes. An opacifier is not necessary for the function of the hair conditioner composition but can impart an enhanced appearance such that the hair conditioning composition looks rich and creamy and not translucent. Examples of suitable opacifiers (as will be appreciated by one of ordinary skill in the art) include, but are not limited to, any of a number of glyceryl monostearates, especially the glyceryl monostearate of the formula $C_{21}H_{42}O_4$, which is commercially available from Lonza, Inc. of Fairlawn, N.J. However, the glyceryl monostearate can be in other forms including the self-emulsified form (identified in the art as "SE") containing sodium and/or potassium stearate. The opacifier (e.g., glyceryl monostearate) is desirably included in the composition in an amount ranging from about 0.1 to about 2% by weight of the composition, preferably from about 0.15% to about 10% by weight of the composition, even more preferably from about 0.15% to about 0.4% by weight of the composition, and still more preferably about 0.25% by weight of the composition.

With respect to the hair strengthener, one example of this optional ingredient is hydrolyzed collagen. If included, the optional hair strengthener desirably is present in an amount ranging from about 0.1% to about 3% by weight of the composition. Other examples of hair strengtheners will be readily apparent to those skilled in the art. Any suitable dyes and/or fragrances (e.g., fruity or floral) can also be included as desired. If included, the optional dyes and/or fragrances are present in an amount ranging from about 0.1% to about 2% by weight of the composition.

The hair conditioner composition of the present invention can have any suitable pH and viscosity. Preferably, the inventive composition exhibits a pH of from about 3 to about 6.5, more preferably from about 4 to 6. The viscosity of the composition of the present invention preferably ranges from about 1,000 cps to about 20,000 cps.

The viscosity of the composition can be determined in bulk and/or as packaged (e.g., as a finished good). In particular, the conditioner composition is made in a large quantity mixing tank, typically in 2,000 gallon batches. Once a batch is made in bulk, the viscosity is typically measured. Preferably, the composition has a viscosity in bulk of from about 1,000 cps to about 4,500 cps, and more preferably from about 1,500 cps to about 3,500 cps.

The bulk conditioner having the desired viscosity is then pumped, subjected to screens, and then the final product is prepared by forcing the conditioner through a nozzle in order to fill the finished goods package (e.g., a 15 oz. container). During this filling process, the viscosity of the conditioner composition typically increases. Preferably, after packaging, the conditioner has a viscosity of from about 2,000 cps to about 8,000 cps, preferably from about 3,500 cps to about 6,000 cps.

The following examples further illustrate the present invention, but, of course, should not be construed as in any way limiting its scope. Quantities are in percent by weight of the total composition, unless otherwise indicated.

EXAMPLE I

This example illustrates exemplary embodiments of the hair conditioning composition of the present invention. The components are added in the order in which they are listed below into a large mixing tank. Components 1–8 below are mixed at a temperature of about 70–80° C. The batch is cooled and components 9 and 10 are added when the temperature is below 40° C. The term "steareth 21" refers to polyoxyethylene (21) stearyl ether. The formulations (varying in the amount of steareth 21) are as follows:

| Base Formula | |
|---|---|
| (1) Water | qs |
| (2) Color | qs |
| (3) Disodium EDTA | 0.03% |
| (4) Steareth 21 | 0.15%–1% |
| (5) Cetyl Alcohol | 2.5% |
| (6) Stearyl Alcohol | 1.5% |
| (7) Stearalkonium Chloride | 1.0% |
| (8) Glyceryl Monostearate | 0.25% |
| (9) DMDM Hydantoin | 0.2% |
| (10) Fragrance (floral) | 0.325% |
| | 100% |

EXAMPLE II (COMPARATIVE EXAMPLE)

This example illustrates a formulation outside the scope of the present invention for comparative purposes. The composition is prepared as described in Example I. The term "Steareth 2" refers to polyoxyethylene (2) stearyl ether. The formulations (varying in the amount of steareth 2) are as follows:

| Base Formula | |
|---|---|
| (1) Water | qs |
| (2) Color | qs |
| (3) Disodium EDTA | 0.03% |
| (4) Steareth 2 | 0.15%–1% |
| (5) Cetyl Alcohol | 2.5% |
| (6) Stearyl Alcohol | 1.2% |
| (7) Stearalkonium Chloride | 1.0% |
| (8) Glyceryl Monostearate | 0.25% |
| (9) DMDM Hydantoin | 0.2% |
| (10) Fragrance (floral) | 0.325% |
| | 100% |

EXAMPLE III

This example compares stability results of compositions of Example I with the comparative compositions of Example II and with a composition absent any steareth (i.e., without any polyoxyethylene stearyl ether). In particular, compositions containing varying concentrations of steareth 21 on the one hand, and varying concentrations of steareth 2 and the composition absent any steareth on the other hand, were tested over time (two weeks, four weeks, eight weeks, and twelve weeks) to determine the amount of pearling (i.e., precipitation) of stearalkonium chloride that took place in the composition at 4° C. Specifically, each formulation was ranked on a scale of zero to ten in terms of the amount of pearling observed at each time interval. For example, a score of zero indicates no pearling and a score of ten indicates maximum pearling. The results are set forth in Table I.

TABLE I

Evaluation Of Sample Pearling With Time Upon Storage at 4° C.

| STEARETH | STEARETH % | 2 WK | 4 WK | 8 WK | 12 WK |
|---|---|---|---|---|---|
| None | — | 2 | 2 | 2 | 2 |
| 21 | 0.15 | 1 | 1 | 1 | 1 |
| 2 | 0.15 | 2 | 3 | 3 | 4 |
| 21 | 0.25 | 1 | 1 | 1 | 1 |
| 2 | 0.25 | 1 | 1 | 5 | 5 |
| 21 | 0.35 | 1 | 1 | 1 | 1 |
| 2 | 0.35 | 2 | 3 | 3 | 4 |
| 21 | 0.50 | 2 | 1 | 1 | 1 |
| 2 | 0.50 | 3 | 5 | 5 | 7 |
| 21 | 1.00 | 0 | 0 | 1 | 1 |
| 2 | 1.00 | 3 | 5 | 7 | 8 |

As seen in Table I, the formulations that contained steareth 21 exhibited surprisingly better results with respect to minimizing pearling, even over time. The steareth 21 containing compositions were also generally smoother and more uniform in appearance.

EXAMPLE IV

This Example compares the amount of fading or discloring exhibited by six different formulations (identified as A–F), as perceived by twelve different observers. Formulations A and C contained no steareth at all. Formulations B and E contained the ingredients set forth in Example I, including 1% steareth 21. Formations D and F contained the ingredients set forth in Example II, including 1% steareth 2. In particular, each formulation was evaluated by twelve observers after twelve weeks following exposure to temperatures of 4° C. and 54° C. cycled through the temperatures. Each observer gave a score on a scale of zero to ten for each formulation. Scores increased from zero to 10 as the perceived fade/discoloration increased. The results are set forth in Table II.

TABLE II

Evaluation Of Color Fading

| | Sample | | | | | |
|---|---|---|---|---|---|---|
| Observer | A | B | C | D | E | F |
| 1 | 7 | 1 | 0 | 7 | 0 | 6 |
| 2 | 6 | 2 | 5 | 3 | 1 | 4 |
| 3 | 8 | 2 | 4 | 6 | 1 | 7 |
| 4 | 8 | 2 | 6 | 8 | 5 | 9 |
| 5 | 6 | 1 | 4 | 3 | 2 | 5 |
| 6 | 8 | 0 | 6 | 2 | 2 | 5 |
| 7 | 8 | 3 | 5 | 6 | 4 | 7 |
| 8 | 9 | 4 | 8 | 7 | 0 | 9 |
| 9 | 10 | 3 | 7 | 2 | 1 | 8 |
| 10 | 7 | 2 | 5 | 5 | 2 | 5 |
| 11 | 7 | 1 | 5 | 2 | 2 | 4 |
| 12 | 3 | 1 | 5 | 3 | 2 | 4 |
| TOTAL | 87 | 22 | 60 | 54 | 22 | 69 |
| Average | 8 | 2 | 5.4 | 5 | 2 | 6.3 |

As seen in Table II, the formulations that contained steareth 21 exhibited the least amount of fade/discoloration. The formulations that contained steareth 2 and no steareth exhibited significant fading.

EXAMPLE V

This example compares the amount of pearling exhibited by the six formulations set forth in Example IV, as perceived by the same observers following the same conditions set forth in Example IV. The scores increase as the pearling increased. The results are set forth in Table III.

TABLE III

Evaluation Of Pearling

| Observer | Sample | | | | | |
|---|---|---|---|---|---|---|
| | A | B | C | D | E | F |
| 1 | 10 | 0 | 0 | 7 | 0 | 6 |
| 2 | 8 | 0 | 0 | 1 | 0 | 1 |
| 3 | 8 | 2 | 4 | 6 | 1 | 7 |
| 4 | 9 | 2 | 0 | 0 | 0 | 0 |
| 5 | 8 | 1 | 4 | 6 | 3 | 5 |
| 6 | 8 | 6 | 7 | 8 | 4 | 7 |
| 7 | 8 | 3 | 5 | 6 | 4 | 7 |
| 8 | 7 | 5 | 8 | 8 | 0 | 4 |
| 9 | 10 | 0 | 0 | 8 | 0 | 5 |
| 10 | 9 | 0 | 4 | 3 | 1 | 8 |
| 11 | 7 | 1 | 2 | 5 | 2 | 4 |
| 12 | 10 | 0 | 5 | 3 | 2 | 5 |
| TOTAL | 102 | 20 | 32 | 61 | 17 | 59 |
| Average | 9.3 | 1.8 | 2.9 | 5.5 | 1.5 | 5.4 |

As seen in Table III, the formulations that contained steareth 21 exhibited the least amount of pearling. The formulations that contained steareth 2 and no steareth exhibited significant pearling.

While this invention has been described with an emphasis upon certain preferred embodiments, it will be apparent to those of ordinary skill in the art that variations in the preferred compositions and methods may be used and that it is intended that the invention may be practiced otherwise than as specifically described herein. Accordingly, this invention includes all modifications encompassed within the spirit and scope of the invention as defined by the following claims.

What is claimed is:

1. An aqueous hair conditioning composition comprising:
   (a) stearalkonium chloride;
   (b) a stabilizing component comprising a polyoxyethylene stearyl ether having more than two oxyethylene units, wherein said polyoxyethylene stearyl ether is present in an amount sufficient to inhibit precipitation of said stearalkonium chloride in said composition; and
   (c) water.

2. The composition of claim 1, wherein said polyoxyethylene stearyl ether is polyoxyethylene (21) stearyl ether.

3. The composition of claim 2, wherein the ratio of stearalkonium chloride to polyoxyethylene (21) stearyl ether is from about 4:1 to about 1:1.

4. The composition of claim 1, wherein water is present in an amount of from about 10% to about 90% by weight of said composition.

5. The composition of claim 1, wherein said stearalkonium chloride is present in an amount of from about 0.2% to about 5% by weight of said composition.

6. The composition of claim 5, wherein stearalkonium chloride is present in an amount of from about 0.5% to about 2.5% by weight of said composition.

7. The composition of claim 6, wherein stearalkonium chloride is present in an amount of from about 0.75% to about 1.5% by weight of said composition.

8. The composition of claim 1, wherein polyoxyethylene stearyl ether is present in an amount of from about 0.1% to about 10% by weight of said composition.

9. The composition of claim 8, wherein polyoxyethylene stearyl ether is present in an amount of from about 0.1% to about 4% by weight of said composition.

10. The composition of claim 9, wherein polyoxyethylene stearyl ether is present in an amount of from about 0.35% to about 1% by weight of said composition.

11. The composition of claim 1, further comprising a preservative, and said preservative is present in an amount of from about 0.1% to about 0.5% by weight of said composition.

12. The composition of claim 11, wherein said preservative is selected from the group consisting of 1,3-dimethylol-5,5-dimetayl hydantoin, disodium EDTA, trisodium EDTA, tetrasodium EDTA, and combinations thereof.

13. The composition of claim 1, further comprising a thickener, and said thickener is present in an amount of from about 0.5% to about 11% by weight of said composition.

14. The composition of claim 13, wherein said thickener is selected from the group consisting of stearyl alcohol, cetyl alcohol, and combinations thereof.

15. The composition of claim 13, wherein said thickener comprises stearyl alcohol and cetyl alcohol, and said stearyl alcohol is present in an amount of from about 0.5% to about 5% by weight of said composition, and said cetyl alcohol is present in an amount of from about 0.5% to about 10% by weight of said composition.

16. The composition of claim 1, further comprising an opacifier.

17. The composition of claim 16, wherein said opacifier is glyceryl monostearate.

18. The composition of claim 1, further comprising a dye.

19. The composition of claim 1, further comprising a fragrance.

20. The composition of claim 1, further comprising a hair strengthener.

21. The composition of claim 20, wherein said hair strenghthener is hydrolyzed collagen.

22. The composition of claim 1, wherein the pH of said composition is from about 3 to about 6.5.

23. The composition of claim 22, wherein the pH of said composition is from about 4 to about 6.

24. The composition of claim 1, wherein the iscosity of said composition is from about 1,000 cps to bout 20,000 cps.

25. The composition of claim 24, wherein the iscosity of said composition is from about 1,500 cps to about 4,500 cps in bulk.

26. The composition of claim 24, wherein the viscosity of said composition is from about 3,500 cps to about 6,000 cps as packaged.

27. An aqueous hair conditioning composition comprising:
   (a) water;
   (b) stearalkonium chloride;
   (c) a stabilizing component comprising a polyoxyethylene stearyl ether having more than two oxyethylene units, wherein said polyoxyethylene stearyl ether is present in an amount sufficient to inhibit precipitation of said stearalkonium chloride in said composition;
   (d) a preservative; and
   (e) a thickener; and, optionally, one or more of the following ingredients:
   (f) a hair strengthener;
   (g) an opacifier;

(h) a dye; and (i) a fragrance.

28. The composition of claim 27, wherein said polyoxyethylene stearyl ether is polyoxyethylene (21) stearyl ether, and said ether is present in an amount of from about 0.1% to about 10% by weight of said composition; said stearalkonium chloride is present in an amount of from about 0.2% to about 5% by weight of said composition; said thickener comprises stearyl alcohol, which is present in an amount of from about 0.5% to about 5% by weight of said composition, and cetyl alcohol, which is present in an amount of from about 0.5% to about 10% by weight of said composition; and wherein said water is present in an amount from about 10% to about 90% by weight of said composition.

29. A method of conditioning hair comprising contacting said hair with the composition of claim 27.

30. A method of conditioning hair comprising contacting said hair with the composition of claim 1.

31. The method of claim 29, wherein said polyoxyethylene stearyl ether is polyoxyethylene (21) stearyl ether.

32. A method of inhibiting the precipitation of stearalkonium chloride in an aqueous stearalkonium chloride-containing hair conditioning composition comprising adding to said composition a polyethylene stearyl ether having a sufficient number of oxyethylene units to inhibit precipitation of stearalkonium chloride in said composition, wherein said polyoxyethylene stearyl ether is present in an amount sufficient to inhibit said precipitation.

33. The method of claim 32, wherein said polyoxyethylene stearyl ether is polyoxyethylene (21) stearyl ether.

34. The composition of claim 1, wherein the polyoxyethylene stearyl ether includes at least 5 oxyethylene units.

35. The composition of claim 1, wherein the polyoxyethylene stearyl ether includes at least 10 oxyethylene units.

36. The composition of claim 1, wherein the polyoxyethylene stearyl ether includes at least 15 oxyethylene units.

37. The composition of claim 1, wherein the polyoxyethylene stearyl ether includes at least 20 oxyethylene units.

* * * * *

UNITED STATES PATENT AND TRADEMARK OFFICE
CERTIFICATE OF CORRECTION

PATENT NO. : 6,187,303
DATED : February 13, 2001
INVENTOR(S) : Dipak K. Ghosh; Rose A. Casanova-Gugliotta; Natalya Gurman It is certified that error appears in the above-identified patent and that said Letters Patent is hereby corrected as shown below:

IN THE CLAIMS:

In Claim 12, Column 8, line 16: "dimetayl" should read --dimethyl--

In Claim 24, Column 8, line 45: "iscosity" should read --viscosity--

In Claim 25, Column 8, line 47: "iscosity" sholud read --viscosity--

Signed and Sealed this

Fifth Day of June, 2001

*Attest:*

*Attesting Officer*

NICHOLAS P. GODICI

*Acting Director of the United States Patent and Trademark Office*

UNITED STATES PATENT AND TRADEMARK OFFICE
CERTIFICATE OF CORRECTION

PATENT NO.   : 6,187,303 B1
DATED        : February 13, 2001
INVENTOR(S)  : Dipak K. Ghosh; Rose A. Casanova-Gugliotta; Natalya Gurman It is certified that error appears in the above-identified patent and that said Letters Patent is hereby corrected as shown below:

<u>Column 7,</u>
Table III, "8" should read -- 1 --.

<u>Column 4,</u>
Line 20, "8" should read -- 1 --.

Signed and Sealed this

Eighteenth Day of September, 2001

Attest:

*Nicholas P. Godici*

NICHOLAS P. GODICI
*Attesting Officer*     *Acting Director of the United States Patent and Trademark Office*